United States Patent [19]
Axelgaard

[11] Patent Number: 5,843,155
[45] Date of Patent: Dec. 1, 1998

[54] CURRENT-CONTROLLING ELECTRODE SYSTEM

[75] Inventor: Jens Axelgaard, Fallbrook, Calif.

[73] Assignee: Axelgaard Manufacturing Company, Ltd., Fallbrook, Calif.

[21] Appl. No.: 873,451

[22] Filed: Jun. 12, 1997

[51] Int. Cl.⁶ .................................................... A61N 1/04
[52] U.S. Cl. ............................................................ 607/152
[58] Field of Search .................................... 607/129, 152, 607/115, 119

[56] References Cited

U.S. PATENT DOCUMENTS

| | | | |
|---|---|---|---|
| 4,736,752 | 4/1988 | Munck et al. | 607/152 |
| 5,269,810 | 12/1993 | Hull et al. | 607/129 |

*Primary Examiner*—Scott M. Getzow
*Attorney, Agent, or Firm*—Walter A. Hackler

[57] ABSTRACT

A transcutaneous medical electrode includes a flexible moderately conductive sheet and a conductive adhesive disposed on one side of the flexible sheet for electrically coupling the flexible sheet to a user's body. A highly conductive grid disposed on another side of the flexible sheet provides an electrical current distribution through the flexible sheet and connective adhesive and into the user's body. The conductive grid includes at least one array of conductive ink lines. Electrical conduction is established with the conductive grid through the use of a second array of conductive ink lines disposed on a flexible non-conductive sheet. An adhesive enables positioning of the flexible non-conductive sheet onto the conductive grid with the conductive ink lines on the flexible non-connective sheet crossing and electrically contacting the conductive grid conductive ink lines in order to modify the current distribution provided by the conductive grid.

13 Claims, 4 Drawing Sheets

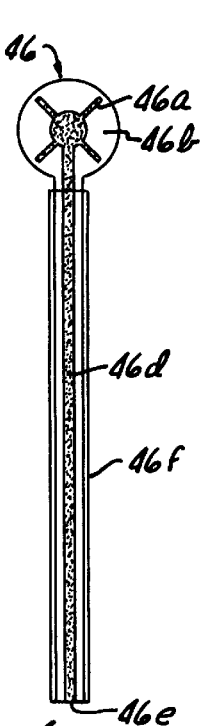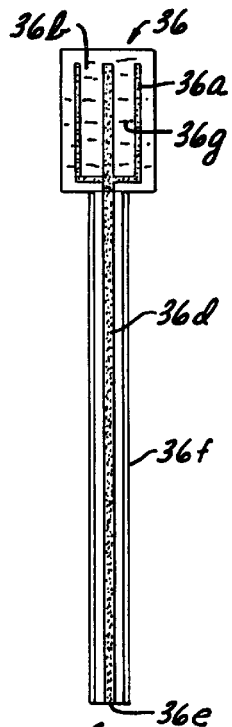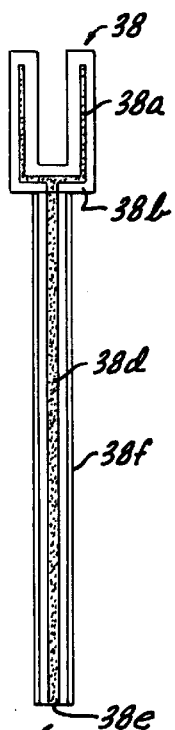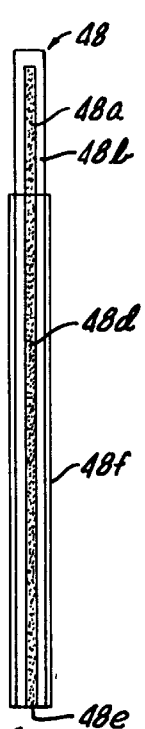
FIG. 4a.   FIG. 4b.   FIG. 4c.   FIG. 4d.
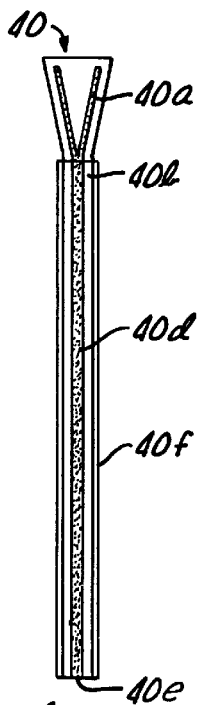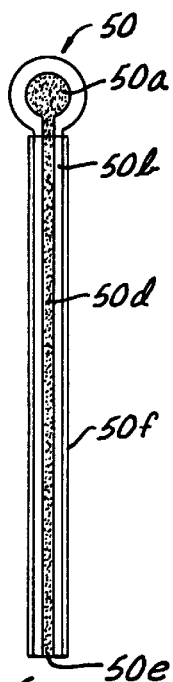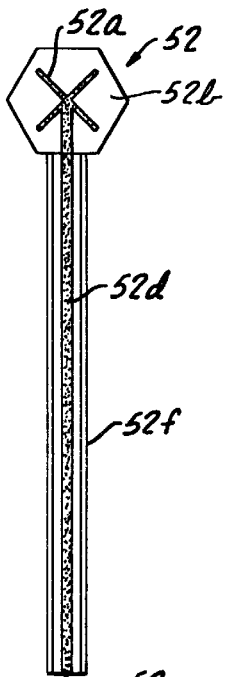
FIG. 4e.   FIG. 4f.   FIG. 4g.

CURRENT-CONTROLLING ELECTRODE SYSTEM

The present invention is generally related to transcutaneous electrodes and is more particularly directed to an electrode configuration for providing improved treatment of physical deficiencies such as, for example, joint swelling, tissue healing, muscle re-education, circulatory impairment, joint dysfunction, and postural disorders.

Nerve and muscle cells are excitable because they are able to discharge action potentials and, accordingly, electrical stimulation of nerve and muscle membranes can evoke such action potential. In order for an action potential to be evoked, the stimulus intensity and pulse duration must be sufficient to pass a threshold. In this regard, muscle membranes require longer pulse durations due to their higher capacitance. Thus, in order to meet this threshold, transcutaneous electrodes must not only be properly placed on the skin but coupled thereto in order to provide sufficient current density to a particular cross-sectional area body tissue current density. This is a very important factor in controlling the reaction of biological tissue to stimulation. As a rule, the greater the current density, the greater the resulting reaction on the tissue.

Earlier electrodes, such as set forth in U.S. Pat. No. 4,736,752, teach the control of current density across an electrode through the use of a conductive ink design area.

Electrode placement is another factor that influences current density and, accordingly, tissue response. This is due to the fact that the impedance of skin, bone, and adipose tissue vary, and, accordingly, placement of electrodes over these tissues will have significant effect on current flow in the surrounding tissues. In addition, orientation of the electrodes can also significantly affect the response of underlying tissue. For example, muscle tissue is nearly four times more conductive in the longitudinal direction of their fibers than in the transverse direction.

In addition, current density at the electrode-tissue interface also depends on the electrode configuration, its ability to conform to a body part, body inflexibility, and a coupling agent to provide low impedance contact between the electrode and the skin surface.

It is accordingly often desirable to provide means for dynamically controlling the current density provided by an electrode. Such dynamic control would enable accommodation not only for misplacement of the electrode in an area designated for stimulation but also to maximize biological response to current pulses provided by the electrode. As hereinabove noted, insufficient current may not cause the expected physiological response. Thus efficient design of current density eliminates unnecessary current which may increase patient discomfort and decrease the efficiency of the electrode.

The present invention is directed to an electrode system which features control of current density which not only enables the electrode to be optimized for current density for a specific application to a tissue but also accommodates for inaccuracies made in placing the electrode upon a skin surface.

SUMMARY OF THE INVENTION

A transcutaneous medical electrode in accordance with the present invention generally includes a flexible sheet with a conductive adhesive disposed on one side of the flexible sheet which provides a means for electrically coupling the flexible sheet to a user's body.

A conductive grid means disposed on another side of the flexible sheet provides an electrical current distribution through the flexible sheet and conductive adhesive into the user's body. The conductive grid means includes at least one array of conductive ink lines disposed, for example, by printing, on the flexible sheet.

Importantly, means are provided for establishing electrical connection with the conductive grid means and for altering the current distribution provided thereby. In this manner, the means for establishing electrical connection provides for greater tailoring of the current distribution provided by the conductive grid means itself.

The means for establishing electrical connection generally includes a flexible non-conductive sheet in an array of conductive ink lines disposed on the flexible non-conductive sheet along with an adhesive which provides a means for positioning the flexible non-conductive sheet onto the conductive grid means with the conductive ink lines on the flexible non-conductive sheet crossing and electrically contacting the conductive grid means conductive ink lines in order to modify the current distribution provided by the conductive grid means.

More particularly in accordance with the present invention, the flexible sheet is electrically conductive. In addition, the second array of conductive ink lines disposed on the flexible non-conductive sheet as well as being connected to a single lead conductive ink line.

Alternatively, the means for establishing electrical connection may comprise a plurality of arrays of conductive ink lines disposed on the flexible non-conductive ink sheet. In this embodiment, each of the plurality of arrays of conductive ink lines are interconnected with each array and to a separate lead conducted ink line for each array.

Alternatively, the means for establishing electrical connection may include a plurality of flexible non-conductive sheets each having an elongate shape and an array of conductive ink lines disposed on each of the plurality of flexible line conductive sheets. In this instance, each of the arrays of conductive ink lines disposed on each of the plurality of flexible non-conductive sheets are connected to a separate lead conductive ink line.

Alternatively, the means for describing electrical connection may be defined as having at least one conductive ink strip disposed on the non-conductive strip. In addition, a flexible non-conductive cover sheet may be provided which overlays the conductive ink strip and exposes one end of the conductive ink strip, with the exposed one end being electrically contacted with the array ink lines of the conductive grid means.

BRIEF DESCRIPTION OF THE DRAWINGS

The advantages and features of the present invention will appear from the following description when considered in conjunction with the accompanying drawings in which:

FIGS. 4a–4g are plan views of various arrays of conductive grid pasterns useful in accordance with the present invention for establishing electrical connection and controlling current distribution.

DETAILED DESCRIPTION

Figure 1:
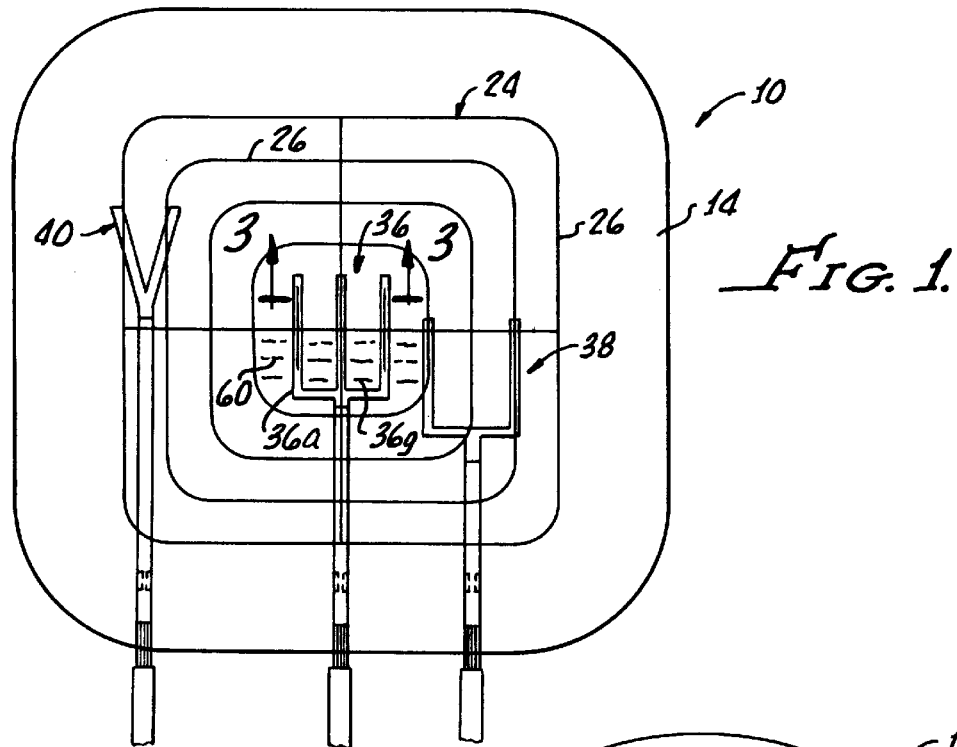
FIG. 1 is a plan view of the transcutaneous medical electrode, in accordance with the present invention, showing a representative conductive grid means disposed on a conductive sheet for controlling current distribution only with a second array of conductive ink lines disposed on a separate sheet which provides a means for establishing electrical connection with the conductive grid means and in addition altering the current distribution provided thereby.
Figure 2:
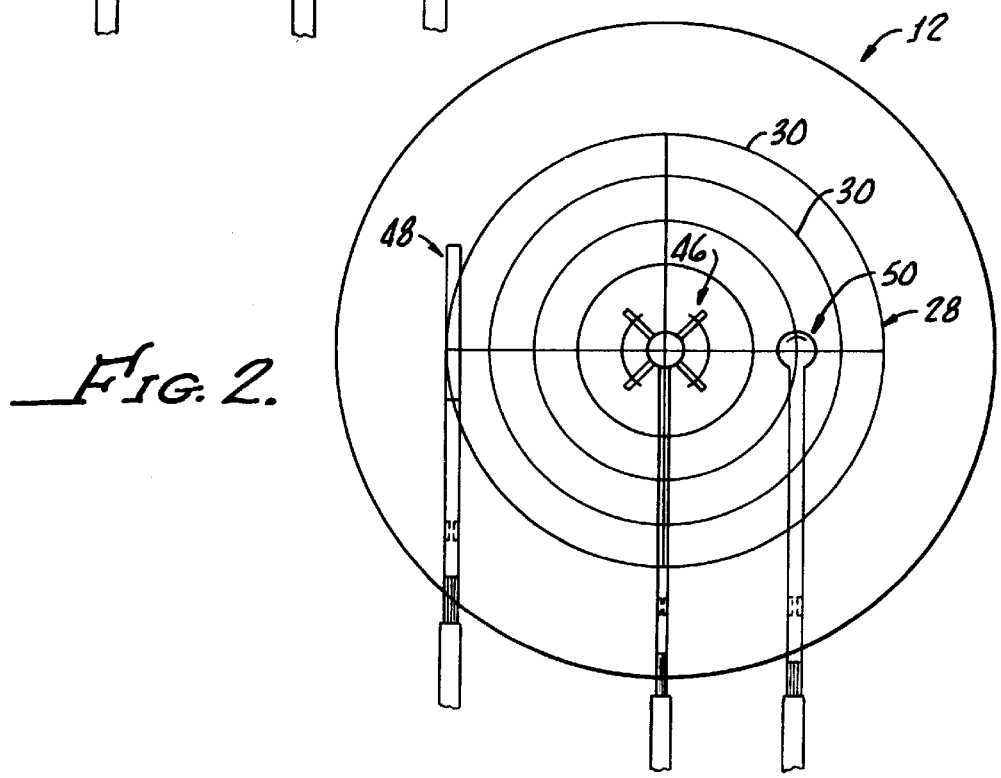
FIG. 2 is a plan view of an alternative embodiment of the present invention showing a circular conductive grid means disposed on a conduction sheet for controlling current distribution along with a representation of various arrays of conductive ink lines disposed on a separate sheet in order to provide electrical connection with the conductive grid means and alter the current distribution provided thereby, the representations herein being presented as illustrating only a few of various patterns which may find use in the present invention and are not presented as being representative of all possible arrangements of conductive lines useful in the present invention.

Turning now to FIGS. 1–2, there is shown electrodes 10, 12 in accordance with the present invention which generally includes a flexible sheet 14, 16, which may be formed from any suitable moderately electrically conductive elastomeric film having suitable surface resistivity of between about $10^3$ ohms/square and about $10^4$ ohms/square, for example, 5000 ohms/square and a transverse resistivity of between about $10^3$ and $10^5$ ohms/square, for example, about $10^4$ ohms/square. Suitable polycarbonate, polyolefin and polyvinylchloride films are available from, for example, 3-M Manufacturing Company and Rexam Graphics. It should be appreciated that while only two geometric configurations, rectangular and circular, are shown herein for the purpose of illustrating the various configurations that the present invention includes, other geometric configurations are to be considered within the scope of the present invention.

Figure 3:
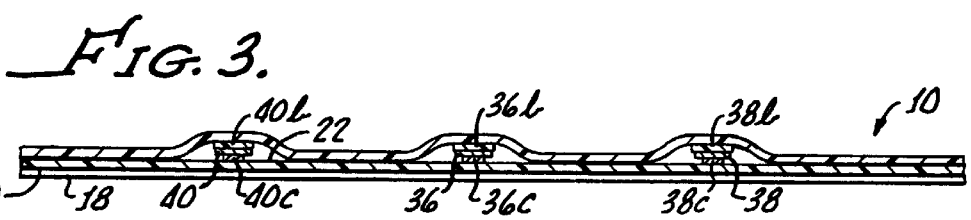
FIG. 3 is cross-section view of the electrode shown in FIG. 1 taken along a line 3—3.

As shown in FIG. 3, a conductive adhesive 18 disposed on one side 20 of the conductive sheet 12 provides a means for electrically coupling the flexible adhesive sheet 12, and electrode 10, to the user's body (not shown in FIGS. 1 and 2). Any suitable conductive adhesive may be utilized such as those manufactured by Valleylab., Inc., Boulder, Colo., or ProCam Medical, Chicopee, Mass. Further details with regard to the assembly of the electrodes 10, 12 may be found in copending U.S. patent application Ser. No. 08/873,450 entitled CURRENT-CONTROLLING ELECTRODE filed on even date herewith and should be incorporated herein in its entirety by this specific reference thereto.

Disposed on another side 22 of the conductive sheet 12 is a highly electrically conductive grid, array, or pattern, 24 which provides a means for controlling current distribution through the flexible moderately conductive sheet 12 and a conductive adhesive 18 into a user's body (not shown). The conductive grid 24 may be formed with conductive ink lines 26 applied to the conductive sheet 12. The conductive ink lines may be formed from any suitable blend of inks including carbon and metal such as silver or copper. Suitable inks are available from Acheson Coloids Company as PTF Flexographic Printable Ink.

It should be appreciated that the conductivity of the conductive grid 24, i.e., ink lines 26, is much greater than the conductivity of the flexible conductive sheet 12 in order to control the current distribution through the conductive sheet 12. For example, with a surface resistivity of about 5000 ohms/square and a transverse resistivity of about $10^4$ for the sheet 12, the resistivity of the ink lines should be about 1 to about 10 ohms/cm.

The difference in conductivity or resistivity between the sheet 12 and the lines 26 enables precise control of current distribution which cannot be achieved, for example, with a non-conductive sheet. In face, ink lines 26 of varied conductivity may be utilized in order to tailor the current through the conductive sheet which may have a thickness of up to about 3 mils, for example, about 1 mil.

Similarly, the electrode 12 shown in FIG. 2 includes a conductive grid 28 with conductive ink lines 30.

Electrification of the conductive grid 24 of electrode 10 is provided by a second array 36 of conductive ink lines 36a disposed on a flexible non-conductive sheet 36b, see also FIG. 4b. A conductive adhesive 36c is provided for positioning the flexible non-conductive sheet 36b onto the conductive grid with the conductive ink lines 30 on the sheet 14 crossing and electrically contacting conductive grid lines 26.

In FIG. 1 various a arrays 36, 38, 40 of conductive lines 36a, 38a, 40a are shown for illustrative purposes. Other arrays 46, 48, 50 with conductive ink lines 46a, 48a, 50a disposed on sheets 46b, 48b, 40b, are shown in FIGS. 2 and 4. An additional exemplary array 52 with lines 52a on sheet 52b is also shown in FIG. 4.

One or more arrays 36, 38, 40, 42, 46, 48, 50, 52 may be utilized to establish electrical connection with the conductive grid 24 or 28 as is shown in FIGS. 1 and 2, with several positions or orientations being indicated in FIGS. 1 and 2.

Figure 5:
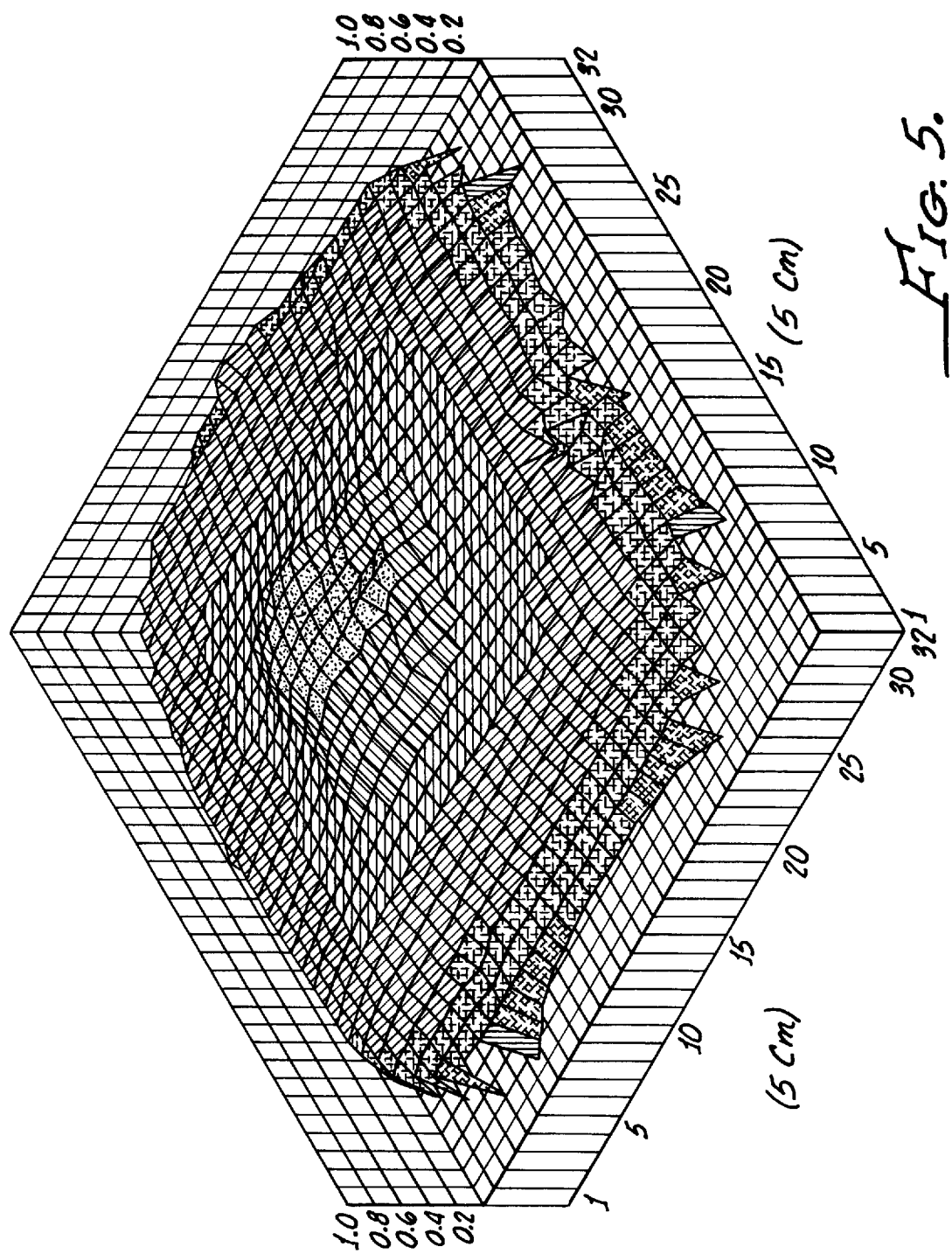
FIG. 5 is a representation of a current density achieved across a skin surface utilizing the electrode shown in FIG. 1 utilizing one of the illustrated second arrays of conductive ink lines for establishing electrical connection and controlling current distribution.
Figure 6:
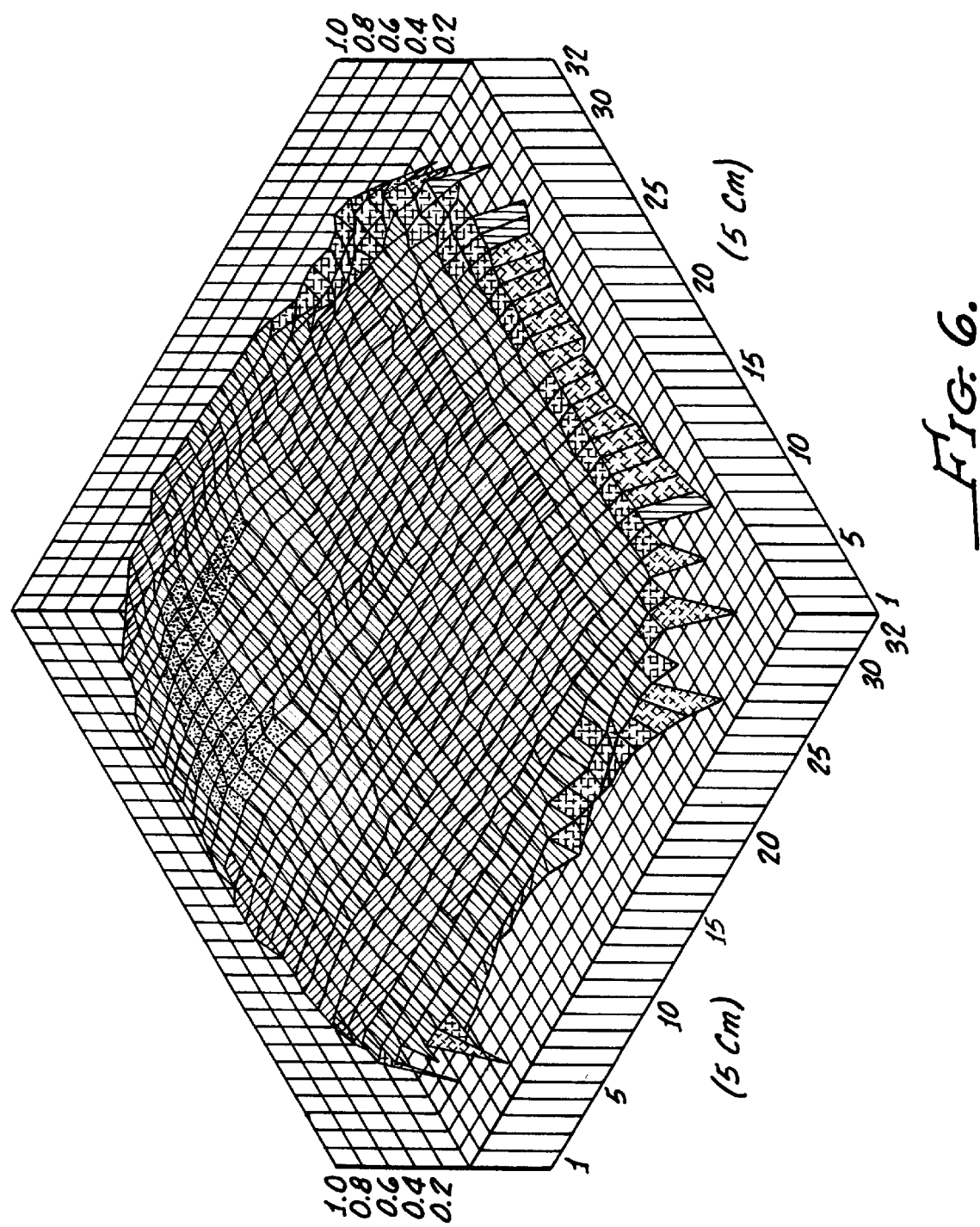
FIG. 6 is a representation of a current density achieved across a skin surface utilizing the electrode shown in FIG. 1 with a different placement or orientation between the conductive grid means and the means for establishing electrical connection therewith.

In this manner, the current distribution provided by the conductive grids 24, 28 may be modified. In that regard, the current distribution provided by the electrode 10 is shown in FIGS. 5 and 6 which illustrate the current distribution over a 5 cm² electrode with two different positions of the array 36 of conductive lines 36a interconnected with the conductive grid 24.

Turning back to FIG. 4 it is preferable that the arrays 36, 38, 40, 46, 48, 50, 52 of ink lines are interconnected and in contact with the single lead ink lines 36d, 38d, 40d, 46d, 48d, 50d, 52d for convenience in connecting ends 36e, 38e, 40e, 46e, 48e, 50e, 52e of the lead conductive ink lines to any suitable electrical conductor to a stimulator, not shown.

More particularly, as shown in FIGS. 4a–4g the lead conductive ink lines, or strip, 36d, 38d, 40d, 46d, 48d, 50d, 52d may be covered by a non-conductive sheets 36f, 38f, 40f, 46f, 48f, 50f, 52f in order to enable only the arrays 36, 38, 40, 46, 48, 50, 52 to be in contact with the conductive grid 24 or 28.

Turning back to FIG. 1 and 4b, abrasive surfaces 60, 36g may be provided on the flexible conductive sheet 12 and the non-conductive sheet 36a respectively, in order to provide a means for inhibiting shear movement between the second array of conductive ink lines 36 and the conductive grid 24 which may occur by inadvertent pulling of the flexible conductive sheet 36.

Although there has been hereinabove described specific transcutaneous medical electrodes, in accordance with the present invention for the purpose of illustrating the manner in which the invention may be used to advantage, it should be appreciated that the invention is not limited thereto. Accordingly, any and all modifications, variations or equivalent arrangements which may occur to those skilled in the art should be considered within the scope of the present invention defined in the appended claims.

What is claimed is:

1. A transcutaneous medical electrode comprising:

a conductive sheet;

conductive adhesive means, disposed on one side of said flexible conductive sheet, for electrically coupling said flexible sheet to a user's body;

conductive grid means, disposed on another side of said flexible conductive sheet, for providing an electrical current distribution through the flexible sheet and conductive adhesive and into the user's body, said conductive grid means comprising at least one array of conductive ink lines; and means for establishing electrical connection with said conductive grid means and for altering the current distribution provided thereby, the means for establishing electrical connection comprising:

a flexible non-conductive sheet;

a second array of conductive ink lines disposed on said flexible non-conductive sheet; and means for positioning said flexible non-conductive sheet onto said conductive grid means with the conductive ink lines on said flexible non-conductive sheet crossing and electrically contacting the conductive grid means conductive ink lines in order to modify the current distribution provided by said conductive grid means.

2. The electrode according to claim 1 wherein said flexible sheet is electrically conductive.

3. The electrode according to claim 2 wherein said second array of conductive ink lines are all interconnected to a single lead conductive ink line.

4. The electrode according to claim 2 wherein the means for establishing electrical connection comprises a plurality of arrays of conductive ink lines disposed in said flexible non-conductive sheet.

5. The electrode according to claim 4 wherein each of the plurality of arrays of said conductive ink lines are interconnected within each array and to a separate lead conductive ink line for each array.

6. The electrode according to claim 2 wherein said means for establishing electrical connection comprises a plurality of flexible non-conductive sheets each having an elongate shape and an array of conductive ink lines disposed on each of the plurality of flexible non-conductive sheets.

7. The electrode according to claim 6 wherein each of the arrays of conductive ink lines disposed on each of the plurality of flexible non-conductive sheets are connected to a separate lead conductive ink lines.

8. The electrode according to claim 1 wherein said means for positioning said flexible non-conductive sheet comprises an adhesive.

9. A transcutaneous medical electrode comprising:

a flexible conductive sheet;

conductive adhesive means, disposed on one side of said flexible conductive sheet, for electrically coupling said flexible conductive sheet to a user's body;

conductive grid means comprising at least one array of conductive ink lines disposed on another side of said flexible conductive sheet, for directing electrical pulses into the user's body; and means for establishing electrical connection with said conductive grid means, said means for establishing comprising:

a flexible non-conductive sheet;

at least one conductive ink sheet disposed on the non-conductive strip;

a flexible non-conductive cover sheet overlaying conductive ink strip and exposing one end of the conductive ink strip, the exposed one end being in electrical contact with said array of conductive ink lines.

10. The electrode according to claim 9 further comprising a second array of conductive ink lines disposed on said flexible non-conductive sheet and in electrical contact with the one end of the conductive ink strip.

11. The electrode according to claim 10 further comprising conductive adhesive for holding the exposed one end of the conductive ink strip and second array of conductive ink lines in control with the conductive grid means.

12. The electrode according to claim 11 further comprising means for inhibiting shear movement between the second array of conductive ink lines and said conductive grid means.

13. The electrode according to claim 12 wherein the means for inhibiting shear movement comprises abrasive surfaces disposed on said flexible conductive sheet and said flexible non-conductive sheet.

* * * * *